(12) United States Patent
Truyen et al.

(10) Patent No.: US 9,014,441 B2
(45) Date of Patent: Apr. 21, 2015

(54) CALIPER FOR MEASURING OBJECTS IN AN IMAGE

(75) Inventors: Roel Truyen, Eindhoven (NL); Joost Frederik Peters, Eindhoven (NL); Roel Van Der Kraan, Utrecht (NL)

(73) Assignee: Koninklijke Philips N.V., Eindhoven (NL)

( * ) Notice: Subject to any disclaimer, the term of this patent is extended or adjusted under 35 U.S.C. 154(b) by 600 days.

(21) Appl. No.: 12/678,496

(22) PCT Filed: Sep. 10, 2008

(86) PCT No.: PCT/IB2008/053646
§ 371 (c)(1),
(2), (4) Date: Mar. 17, 2010

(87) PCT Pub. No.: WO2009/037616
PCT Pub. Date: Mar. 26, 2009

(65) Prior Publication Data
US 2010/0260383 A1 Oct. 14, 2010

(30) Foreign Application Priority Data

Sep. 17, 2007 (EP) ..................................... 07116529

(51) Int. Cl.
*G06K 9/00* (2006.01)
*A61B 5/107* (2006.01)
(Continued)

(52) U.S. Cl.
CPC .............. *A61B 5/1072* (2013.01); *G06T 7/0012* (2013.01); *G06T 7/602* (2013.01); *G06T 19/00* (2013.01); *G06T 2219/012* (2013.01)

(58) Field of Classification Search
CPC .... A61B 5/1072; G06T 7/0012; G06T 7/602; G06T 19/00
USPC ......... 382/100, 128–133, 154, 162, 164–165, 382/168, 170–173, 180–181, 190, 195, 199, 382/217, 224, 225, 227, 256, 270–273, 288, 382/296, 307–308; 128/920, 922–925; 378/8, 37, 62; 345/157, 619; 600/426
See application file for complete search history.

(56) References Cited

U.S. PATENT DOCUMENTS 5,400,513 A 3/1995 Duffield
6,939,301 B2 * 9/2005 Abdelhak .................... 600/437
(Continued)

FOREIGN PATENT DOCUMENTS

WO 2005022464 A1 3/2005
WO 2007008340 A1 1/2007

OTHER PUBLICATIONS

Srinath C. Yeshwant, BS, Ronald M. Summers, MD, PhD, Jianhua Yao, PhD, Daniel S. Brickman, BS, J. Richard Choi, ScD, MD and Perry J. Pickhardt,MD, "Polyps: Linear and Volumetric Measurement at CT Colonography", Radiological Society of North America, vol. 241, No. 3 Dec. 2006, pp. 802-811, XP002535793.*
(Continued)

*Primary Examiner* — Hadi Akhavannik

(57) ABSTRACT

The invention relates to a system (300) for performing and visualizing a measurement of an object viewed in an image computed from image data, the system comprising an image unit (310) for visualizing the image data in the image for displaying in a display, a deployment unit (320) for deploying a caliper (21; 22; 23; 24) in an image data space based on the location of the object in the image data space, and a caliper unit (330) for visualizing the caliper (21; 22; 23; 24) in the image, wherein the caliper (21; 22; 23; 24) comprises a first planar surface (211) and a second planar surface (212) substantially parallel to the first planar surface (211), and wherein the measurement of the object is determined based on the distance between the planes of the first and second planar surface. Viewing the first and second planar surfaces of the caliper, visualized together with the measured object, improves the visualization of the measurement of an anatomical or pathological structure, because the first and second planar surface help a user to relate the measurement to the object—to see what is being measured. Advantageously, in an embodiment of the system (300), manually aligning the first and second planar surface with the object may also improve capturing the size of the object, because the system makes the measurement both easier to obtain and more accurate.

9 Claims, 9 Drawing Sheets

(51) Int. Cl.
　　　*G06T 7/00*　　(2006.01)
　　　*G06T 7/60*　　(2006.01)
　　　*G06T 19/00*　(2011.01)

(56) References Cited

U.S. PATENT DOCUMENTS

| | | | |
|---|---|---|---|
| 7,327,857 B2* | 2/2008 | Lloyd et al. | 382/106 |
| 7,333,644 B2* | 2/2008 | Jerebko et al. | 382/128 |
| 7,876,939 B2* | 1/2011 | Yankelevitz et al. | 382/128 |
| 8,055,047 B2* | 11/2011 | Sundaram et al. | 382/131 |
| 2002/0028006 A1 | 3/2002 | Novak et al. | |
| 2002/0131625 A1* | 9/2002 | Vining et al. | 382/128 |
| 2003/0026473 A1* | 2/2003 | Lee et al. | 382/152 |
| 2003/0048936 A1 | 3/2003 | Fan et al. | |
| 2004/0252870 A1* | 12/2004 | Reeves et al. | 382/128 |
| 2005/0201611 A1* | 9/2005 | Lloyd et al. | 382/152 |
| 2006/0034538 A1* | 2/2006 | Potter et al. | 382/256 |
| 2006/0285730 A1* | 12/2006 | Habets et al. | 382/128 |
| 2008/0144917 A1* | 6/2008 | Liu et al. | 382/141 |
| 2008/0214960 A1* | 9/2008 | Hodgson et al. | 600/587 |
| 2008/0240532 A1* | 10/2008 | Carneiro et al. | 382/131 |
| 2010/0215245 A1* | 8/2010 | Olivan Bescos | 382/133 |
| 2010/0222684 A1* | 9/2010 | Hatzilias et al. | 600/476 |

OTHER PUBLICATIONS

Pickhardt et al:"Linear Polyp Measurement at CT Colonography: In Vitro and In Vivo Comparison of Two-Dimensional and Three-Dimensional Displays"; Radiology 2005, vol. 236, pp. 872-878.

Gopalswamy et al: "Is In Vivo Measurement of Size of Polyps During Colonoscopy Accurate?"; Gastrointestinal Endoscopy 1997, vol. 46, No. 6, pp. 497-502.

Yeshwant et al: "Polyps: Linear and Volumetric Measaurement at CT Colonography"; Radiology, Dec. 2006, vol. 241, No. 3, pp. 802-811.

Bielen et al: "Computer-Aided Detection for CT Colonography: Update 2007"; Abdominal Imaging, Aug. 10, 2007, vol. 32, pp. 571-581.

Anonymous: "Measurement & Analysis for Biomedical Applications"; Feb. 11, 2007, Retrieved from the Internet at http://web.archive.org/web/20070211124134/wwwpaxit.com/pdfs/PAXit_Biomedical.pdf> on Jun. 6, 2009, 2 page document.

Taylor et al:"CT Colonography: Automated Measurement of Colonic Polyps Compared With Manual Techniques—Human In Vitro Study"; Radiology, Jan. 2007, vol. 242, No. 1, pp. 120-128.

Burling et al: "CT Colonography; Automatic Measurement of Polyp Diameter Compared With Manual Assessment—An In-Vivo Study"; Clinical Radiology, 2007, vol. 62, pp. 145-151.

Dijkers et al: "Segmentation and Size Measurement of Polyps in CT Colonography"; Medical Image Computing and Computer-Assisted Intervention (MICCAI Jan. 1, 2005), LNCS, vol. 3749, pp. 712-719.

Preim et al: "Integration of Measurement Tools in Medical 3d Visualizations"; IEEE Visualization 2002 Proceedings, Oct. 27-Nov. 1, 2002, Boston, MA., IEEE, Nov. 2002, pp. 21-28.

Hastreiter et al: "Fast Analysis of Intracranial Aneurysms Based on Interactive Direct Volume Rendering and CTA"; Medical Image Computing and Computer-Assisted Intervention (MICCAI 1998), LNCS 1496, pp. 660-669.

Summers et al: "Automated Polyp Detector for CT Colonography: Feasibility Study"; Radiology 2000, vol. 216, pp. 284-290.

North Dakota Archeology Technologies Laboratory: "Virtual Caliper Tools"; Retrieved from the Internet at http://atl.ndsu.edu/grants/eai/calipers.htm; Retrieved on Mar. 6, 2007.

Foley et al: "Computer Graphics: Principles and Practice"; Addison-Wesley Publishing Company, 1996, Chapter 18.

* cited by examiner

CALIPER FOR MEASURING OBJECTS IN AN IMAGE

FIELD OF THE INVENTION

The invention relates to the field of image analysis and, more specifically, to measuring structures viewed in images.

BACKGROUND OF THE INVENTION

Computed Tomography (CT) colonoscopy, also known as virtual colonoscopy, is a technique for detecting polyps in the colon. Colon cancer is often preceded by the presence of a benign polyp before it becomes malignant. The size of a polyp is important because it helps predict the likelihood of malignancy. The measured size of a polyp in CT colonography images is used to determine the action a patient has to undergo after examination.

Currently, the polyp size on two-dimensional (2D) or three-dimensional (3D) colonography images may be measured manually by measuring the distance between two points placed at two locations on the polyp base visualized in an image. The CT colonography software computes the Euclidean distance between the two points. When using a 2D image to perform the measurement, e.g., on an axial or multiplanar reformatted image, each point is placed on the colon wall somewhere halfway between the black (the colon air) and the white (the colon wall) gray value. In 3D, the points are positioned directly on the visible colon surface. The polyp size is determined on the basis of the distance of the two points. A manual measurement technique for measuring the polyp size is described by P. J. Pickhardt et al. in an article entitled "Linear polyp measurement at CT colonography: In vitro and in vivo comparison of two-dimensional and three-dimensional displays", published Radiology, vol. 236 (2005), no. 3, pages 872-878. In automatic measurements, the size of the polyp is computed based on image data segmentation results. An automatic measurement technique for measuring the polyp size is described by D. Burling et al. in an article entitled "Ct colonography: Automatic measurement of polyp diameter compared with manual assessment—an in-vivo study", published in Clinical Radiology 62 (2007), pages 145-151.

The polyp size is visualized by a line segment defined by the two points in a manual approach or floating inside the colon wall or in the air above the polyp in an automatic approach. This way of visualizing the measured polyp size does not always show the relationship between the measurement and the measured object.

Further, in a manual approach, the measured size of the object may be less accurate. FIG. 1A schematically illustrates a manually measured polyp size according to prior art. In a top view 11, two points 101 and 102 are selected on a contour 100 which is assumed to represent a projection of the polyp on a plane perpendicular to the viewing direction. The distance D1 between the selected two points 101 and 102 is accepted as the size of the polyp. However, in a side view 12 of the polyp one can see that the distance D1 does not coincide with the size of the contour 100.

SUMMARY OF THE INVENTION

It would be advantageous to have a system that improves visualizing a measurement of an anatomical or pathological structure.

To better address this issue, in an aspect of the invention, a system for performing and visualizing a measurement of an object viewed in an image computed from image data is provided, the system comprising:
   an image unit for visualizing the image data in the image for displaying in a display;
   a deployment unit for deploying a caliper in an image data space based on the location of the object in the images data space; and
   a caliper unit for visualizing the caliper in the image;
wherein the caliper comprises a first planar surface and a second planar surface, substantially parallel to the first planar surface, and wherein the measurement of the object is determined based on the distance between the planes of the first and second planar surface.

Viewing the first and second planar surfaces of the caliper, visualized together with the measured object, improves the visualization of the measurement of an anatomical or pathological structure, because the first and second planar surface help a user to relate the measurement to the object.

In an embodiment, the system further comprises a manipulation unit for manipulating the caliper in the image data space. Manipulations comprise translations, rotations and scaling of the caliper. Scaling of the caliper may be isotropic or directional. The manipulations allow to better position the caliper relative to the object and may thus improve performing the measurement, because it is easier to see what is being measured. Advantageously, the size of the object measured by the system of the invention is often more accurate. FIG. 1B schematically illustrates a manually measured polyp size according to the invention. In a top view 11, the first and second surface 211 of the caliper and 212, respectively, is adjacent to a contour 100 which is assumed to represent a projection of the polyp on a plane perpendicular to the viewing direction. The distance D2 between the two surfaces 211 and 212 is accepted as the size of the polyp. This is in agreement with a definition of the polyp size described in an article by N. Gopalswamy et al., entitled "Is in vivo measurement of size of polyps during colonoscopy accurate?", published in Gastrointestinal Endoscopy 46 (1997), no. 6, pages 497-502. A side view 12 further illustrates the distance D2 measured by the caliper of the invention.

In an embodiment of the system, the first or second planar surface is semi-transparent. Semi-transparent planar surfaces allow viewing the object and other anatomical structures displayed in an image computed from the image data by the image unit through the first and second planar surface.

In an embodiment of the system, the caliper further comprises a caliper axis. The caliper axis may be a rotation axis of the caliper. The caliper axis may further improve aligning the caliper with the measured object, in particular with an object having its own axis.

In an embodiment of the system, the deployment unit is further arranged for aligning the caliper axis with an axis of the object. This makes aligning the caliper with an axis of the object, e.g., with a colon polyp axis, easier for the user of the system.

In an embodiment, the system is used for measuring a colon polyp in a colonoscopic CT image. Advantageously, the system has proved very useful in test measurements of colon polyps in colonoscopic CT images.

In a further aspect of the invention, the system according to the invention is comprised in an image acquisition apparatus.

In a further aspect of the invention, the system according to the invention is comprised in a workstation.

In a further aspect of the invention, a method of performing and visualizing a measurement of an object viewed in an image computed from image data is provided, the method comprising:

an image step for visualizing the image data in the image for displaying in a display;

a deployment step for deploying a caliper in an image data space based on the location of the object in the images data space; and a caliper step for visualizing the caliper in the image;

wherein the caliper comprises a first planar surface and a second planar surface, substantially parallel to the first planar surface, and wherein the measurement of the object is determined based on the distance between the planes of the first and second planar surface.

In a further aspect of the invention, a computer program product to be loaded by a computer arrangement is provided, the computer program product comprising instructions for performing and visualizing a measurement of an object viewed in an image computed from image data, the computer arrangement comprising a processing unit and a memory, the computer program product, after being loaded, providing said processing unit with the capability to carry out the following tasks:

visualizing the image data in the image for displaying in a display;

deploying a caliper in an image data space based on the location of the object in the images data space; and visualizing the caliper in the image;

wherein the caliper comprises a first planar surface and a second planar surface, substantially parallel to the first planar surface, and wherein the measurement of the object is determined based on the distance between the planes of the first and second planar surface.

It will be appreciated by those skilled in the art that two or more of the above-mentioned embodiments, implementations, and/or aspects of the invention may be combined in any way deemed useful.

Modifications and variations of the image acquisition apparatus, of the workstation, of the method, and/or of the computer program product, which correspond to the described modifications and variations of the system, can be carried out by a skilled person on the basis of the present description.

The skilled person will appreciate that the system may be applied to view reports comprising multidimensional image data, e.g., 2-dimensional, 3-dimensional, or 4-dimensional images, acquired by various acquisition modalities such as, but not limited to, standard X-ray Imaging, Computed Tomography (CT), Magnetic Resonance Imaging (MRI), Ultrasound (US), Positron Emission Tomography (PET), Single Photon Emission Computed Tomography (SPECT), Digital Tomosynthesis, and Nuclear Medicine (NM).

BRIEF DESCRIPTION OF THE DRAWINGS

These and other aspects of the invention will become apparent from and will be elucidated with respect to the implementations and embodiments described hereinafter and with reference to the accompanying drawings, wherein.

Identical reference numerals are used to denote similar parts throughout the Figures.

DETAILED DESCRIPTION OF EMBODIMENTS

Figure 1A:
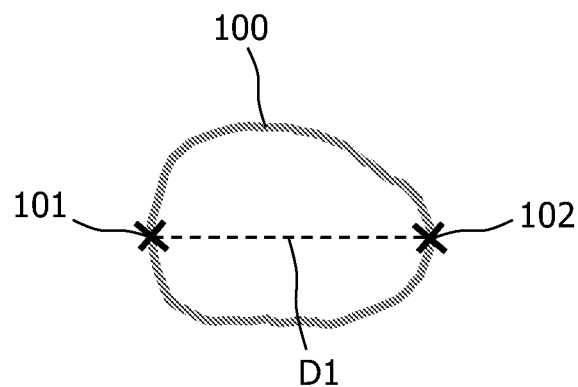
FIG. 1A schematically illustrates a manually measured polyp size according to prior art.
Figure 1A:
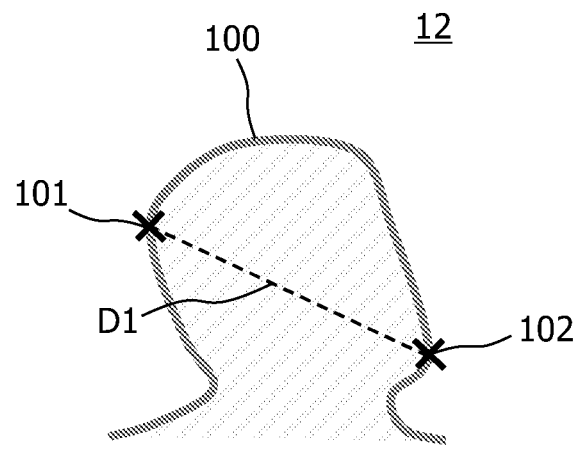
Figure 1B:
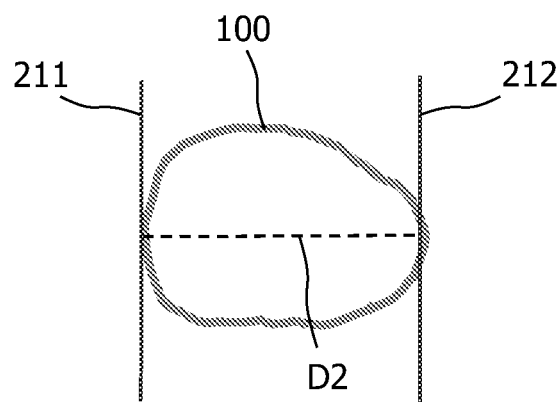
FIG. 1B schematically illustrates a manually measured polyp size according to the invention.
Figure 1B:
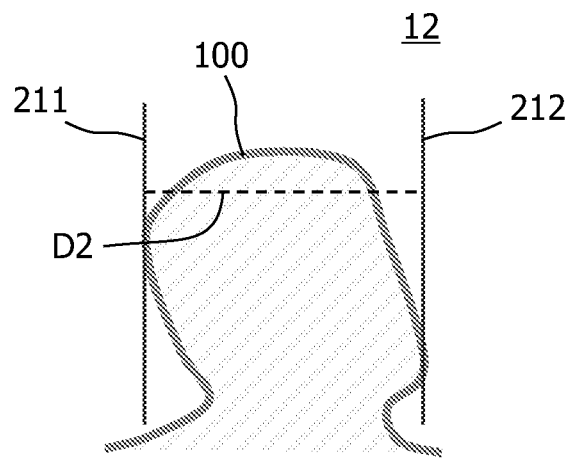
Figure 2:
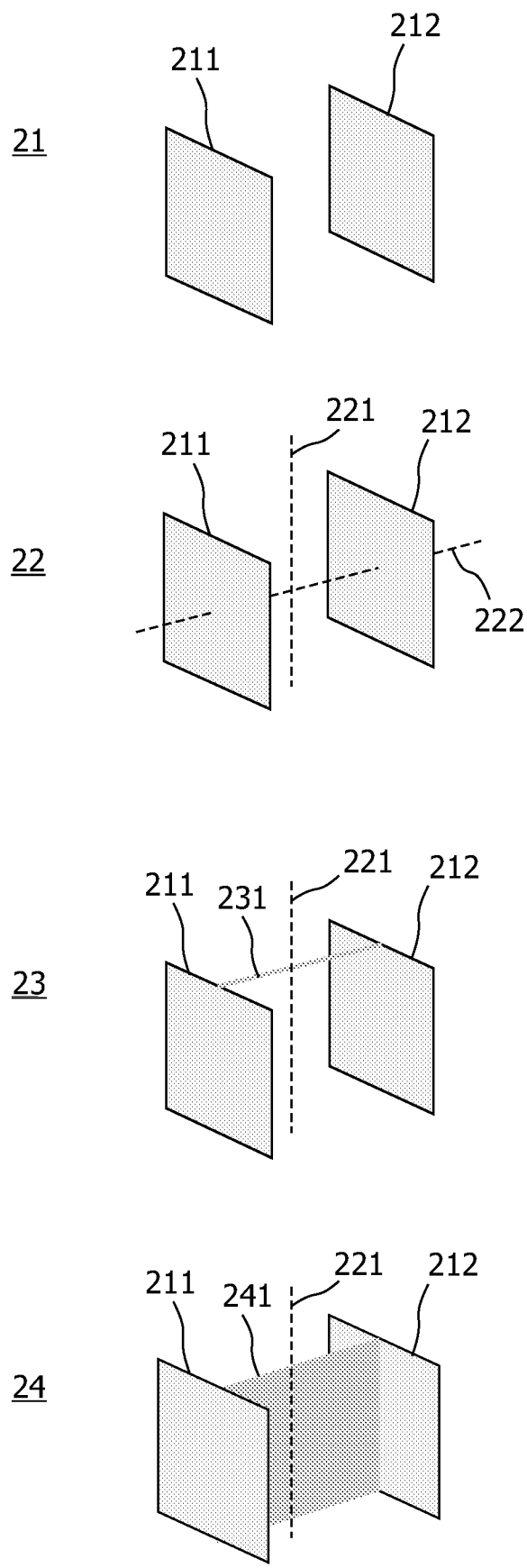
FIG. 2 illustrates exemplary embodiments of the caliper of the invention.

FIG. 2 illustrates exemplary embodiments of the caliper of the invention. A first embodiment 21 of the caliper comprises a first planar surface 211 and a second planar surface, substantially parallel to the first planar surface 212. The first and second planar surface are both a rectangle. The rectangles are aligned with each other, i.e., the line determined by a pair of corresponding vertices of the first and second planar surface is substantially perpendicular to the first and second planar surface. The skilled person will understand that other shapes and/or alignments are also possible and that the scope of the invention is not limited by the shape and alignment of the first and second planar surface used to illustrate the invention. For example, in an embodiment, the first and second planar surface may be a triangle or a circle. In an embodiment, a circle of the first planar surface may have a radius different from, or may be not coaxial with, a circle of the second planar surface. A size of the object is determined based on the distance between the planes of the first and second planar surface.

A second embodiment 22 of the caliper comprises a first caliper axis 221 and a second caliper axis 222. The first caliper axis 221 is substantially parallel to the first and second planar surface and placed substantially in the middle between the two planar surfaces. The second caliper axis 222 is defined by the centers of the first and second planar surface. The first and/or second caliper axis 221 and/or 222, respectively, may or may not be visualized in an image. The first and second caliper axis 221 and/or 222, respectively, may be helpful in aligning the caliper with an anatomical or pathological structure such as a colon polyp.

A third embodiment 23 of the caliper comprises a line segment 231. The ends of the line segment 231 are the centers of the top sides of the rectangles of the first and second planar surface 211 and 212. The line segment 231 is perpendicular to the first and second planar surface and may be useful for visualizing the size of the measured object.

A fourth embodiment 24 of the caliper comprises a third rectangular surface 241 substantially perpendicular to the first and second planar surface. The vertices of this rectangle are the centers of the top and bottom side of the rectangles of the first and second planar surface.

The skilled person will appreciate that other structural or functional elements may be added to the described embodiments of the caliper. These elements may further improve performance and/or visualization of the caliper.

Figure 3:
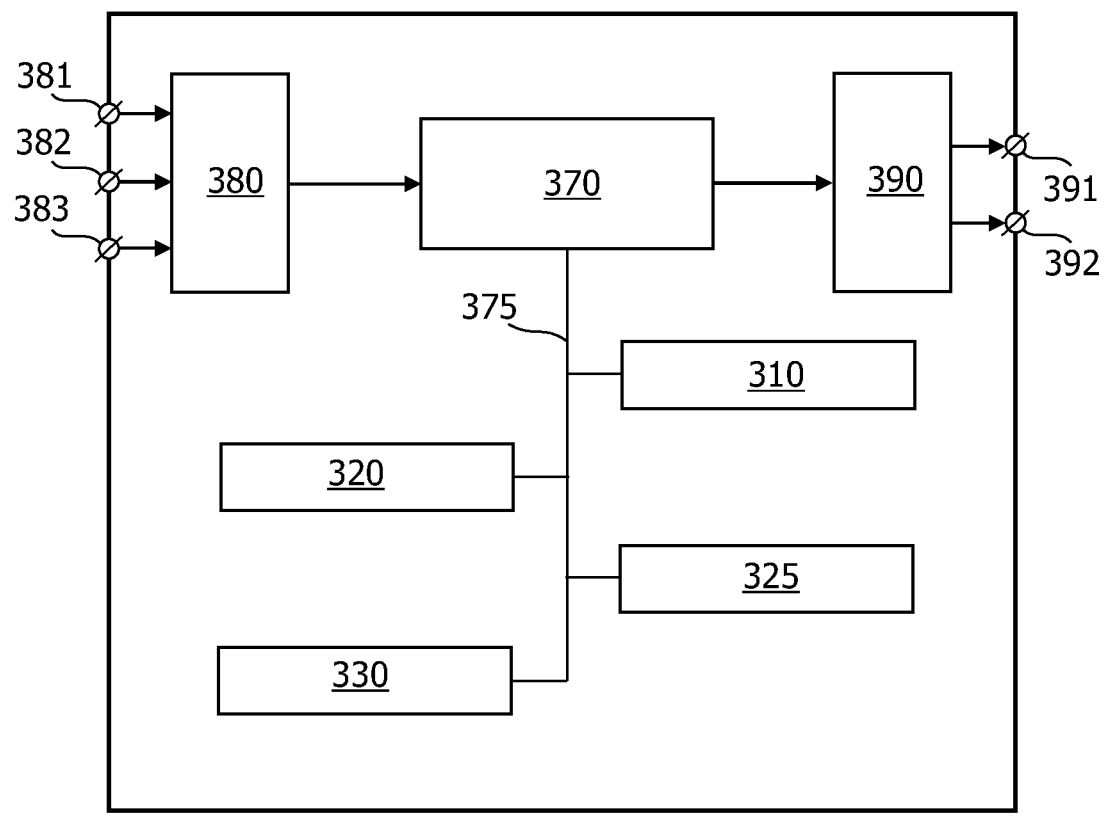
FIG. 3 schematically shows a block diagram of an exemplary embodiment of the system.

FIG. 3 schematically shows a block diagram of an exemplary embodiment of the system 300 for performing and visualizing a measurement of an object viewed in an image computed from image data, the system comprising:

an image unit 310 for visualizing the image data in the image for displaying in a display;

a deployment unit 320 for deploying a caliper in an image data space based on the location of the object in the images data space; and a caliper unit 330 for visualizing the caliper in the image;

wherein the caliper comprises a first planar surface 211 and a second planar surface 212 substantially parallel to the first planar surface, and wherein the measurement of the object is determined based on the distance between the planes of the first and second planar surface.

The exemplary embodiment of the system 300 further comprises the following units:
a manipulation unit 325 for manipulating the caliper in the image data space; and
a memory unit 370 for storing data.

In an embodiment of the system 300, there are three input connectors 381, 382 and 383 for the incoming data. The first input connector 381 is arranged to receive data coming in from a data storage means such as, but not limited to, a hard disk, a magnetic tape, a flash memory, or an optical disk. The second input connector 382 is arranged to receive data coming in from a user input device such as, but not limited to, a mouse or a touch screen. The third input connector 383 is arranged to receive data coming in from a user input device such as a keyboard. The input connectors 381, 382 and 383 are connected to an input control unit 380.

In an embodiment of the system 300, there are two output connectors 391 and 392 for the outgoing data. The first output connector 391 is arranged to output the data to a data storage means such as a hard disk, a magnetic tape, a flash memory, or an optical disk. The second output connector 392 is arranged to output the data to a display device. The output connectors 391 and 392 receive the respective data via an output control unit 390.

The skilled person will understand that there are many ways to connect input devices to the input connectors 381, 382 and 383 and the output devices to the output connectors 391 and 392 of the system 300. These ways comprise, but are not limited to, a wired and a wireless connection, a digital network such as, but not limited to, a Local Area Network (LAN) and a Wide Area Network (WAN), the Internet, a digital telephone network, and an analog telephone network.

In an embodiment of the system 300, the system 300 comprises a memory unit 370. The system 300 is arranged to receive input data from external devices via any of the input connectors 381, 382, and 383 and to store the received input data in the memory unit 370. Loading the input data into the memory unit 370 allows quick access to relevant data portions by the units of the system 300. The input data may comprise, for example, the image data. The memory unit 370 may be implemented by devices such as, but not limited to, a Random Access Memory (RAM) chip, a Read Only Memory (ROM) chip, and/or a hard disk drive and a hard disk. The memory unit 370 may be further arranged to store the output data. The output data may comprise, for example, data for displaying the caliper. The memory unit 370 may be also arranged to receive data from and deliver data to the units of the system 300 comprising the image unit 310, the deployment unit 320, the manipulation unit 325, and the caliper unit 330, via a memory bus 375. The memory unit 370 is further arranged to make the output data available to external devices via any of the output connectors 391 and 392. Storing data from the units of the system 300 in the memory unit 370 may advantageously improve performance of the units of the system 300 as well as the rate of transfer of the output data from the units of the system 300 to external devices.

Alternatively, the system 300 may comprise no memory unit 370 and no memory bus 375. The input data used by the system 300 may be supplied by at least one external device, such as an external memory or a processor, connected to the units of the system 300. Similarly, the output data produced by the system 300 may be supplied to at least one external device, such as an external memory or a processor, connected to the units of the system 300. The units of the system 300 may be arranged to receive the data from each other via internal connections or via a data bus.

The image unit 310 of the system 300 is arranged for visualizing the image data in the image for displaying on a display. The tasks to be performed by the image unit 310 include, for example, determining a viewport for displaying the image. The skilled person will know typical functions, which can be implemented in embodiments of the image unit 310.

There are many ways of computing a view of a 3D region of image data space. The view may be computed using, for example, maximum intensity projection (MIP), iso-surface projection (ISP), and direct volume rendering (DVR). In MIP, a 3D location of maximum intensity along a projection ray is found. The ray is cast from a viewing plane. The intensity value of the pixel on the viewing plane may be set to the found maximum intensity value along the ray. In ISP, projection rays are terminated when they cross the iso-surface of interest. The iso-surface is defined as the level set of the intensity function, i.e. the set of all voxels having the same intensity value. More information on MIP and ISP can be found in a book by Barthold Lichtenbelt, Randy Crane, and Shaz Naqvi, entitled "Introduction to Volume Rendering", published by Hewlett-Packard Professional Books, Prentice Hall; Bk&CD-Rom edition (1998). In DVR, a transfer function assigns a renderable property, such as opacity, to intensity values comprised in the image data. An implementation of DVR is described in an article by T. He et al, entitled "Generation of Transfer Functions with Stochastic Search Techniques" in Proceedings of IEEE Visualization, pages 227-234, 1996.

Objects such as iso-surfaces may be identified in the image data and may be used to define objects in model coordinate systems of a graphics processor. A graphics pipeline of the graphics processor may be used to compute the view of the objects comprised in the model coordinate systems. The graphics pipeline is described in a book by J. D. Foley et al, entitled "Computer graphics: Principles and practice", $2^{nd}$ Ed., Addison-Wesley, Reading, Mass., USA, 1996.

The skilled person will understand that there are many methods that may be employed for computing a view of a 3D region of image data space. The choice of the method of computing the view of the 3D region of the image data space does not limit the scope of the claims.

The deployment unit 320 of the system is arranged for deploying a caliper in an image data space. In an embodiment of the system 300, the caliper is deployed in a pre-defined location of the image data space or in a location specified by the user. Optionally, the deployment unit 320 may be arranged to receive a user input for specifying a caliper of a plurality of calipers for deployment.

In an embodiment of the system 300, the deployment unit 320 is arranged for segmenting the image data and deploying the caliper based on the image data segmentation. A method of segmenting, for example, a colon polyp is described by J. J. Dijkers et al. in an article entitled "Segmentation and size measurement of polyps in ct colonography, published in "Medical image computing and computer-assisted intervention-MICCAI 2005, pt. 1, vol. 3749, 2005, pp. 712-719, hereinafter referred to as Ref. 1. The size of the polyp can be also computed using the method described in Ref. 1. Optionally, there may be a separate segmentation unit for segmenting the image data, comprised in the system 300.

In an embodiment of the system 300, the deployment unit 320 is arranged to determine the colon polyp axis based on the segmentation results and to align an axis of the caliper with the determined colon polyp axis. Ref 1 describes how to determine the colon polyp axis. The colon polyp axis may be defined by two points, the polyp mean point and the polyp center point. The polyp mean point is computed by taking the mean of all points obtained in the polyp segmentation; the polyp center point is derived by minimizing the sum of distances of a point to all the surface normals.

In an embodiment of the system 300, the deployment unit 320 is further arranged to compute the size of the polyp and rotate and scale the aligned caliper based on the image data segmentation, using the method described in Ref. 1, for example.

The optional manipulation unit 325 is needed when measuring the size of the organ is performed manually. In an embodiment of the system 300, after the caliper has been deployed, the manipulation unit 325 is arranged to receive a user input from a user input device, such as a mouse, a trackball, or a keyboard, for example. The manipulation unit may be further arranged to translate, rotate, and/or scale the caliper based on the user input.

In an embodiment of the system 300, the manipulation unit 325 is arranged for translating the caliper in the image data space. The manipulation unit 325 is arranged to compute the translated location of the caliper on the basis of the user input. In an embodiment, the translation vectors are substantially parallel to the viewing plane. In another embodiment, the user may be also able to zoom in and out the caliper, when a perspective projection technique is used to compute the view of the region of the image data space.

In an embodiment of the system 300, the manipulation unit 325 is arranged for rotating the caliper in the image data space. Any number of rotation axes may be implemented. A rotation axis may be one of the three Cartesian axes of a reference system in the image data space. Alternatively, a rotation axis may be an axis of the caliper. For each rotation, a rotation axis and/or angle are selected by the user, and user input data specifying the rotation axis and/or angle is obtained by the manipulation unit 325.

In an embodiment of the system 300, the manipulation unit 325 is arranged for scaling the caliper by a scaling factor in a direction in the image data space. Scaling of the caliper may be isotropic or anisotropic. For example, scaling of the caliper may be defined in a direction substantially perpendicular to the first and second planar surface. In this case, the scaling factor determines the distance between the first and second planar surface. In the case of isotropic scaling of the caliper, both the distance between the two planar surfaces and the size of the first and second planar surface are scaled. In this case too, the scaling factor determines the distance between the first and second planar surface. Scaling of a 3D caliper may occur in a plurality of directions. Optionally, a plurality of scaling factors may be determined, e.g., one scaling factor for each scaling direction. Optionally, the mode of scaling may be selectable and may be determined by the user.

Figure 4:
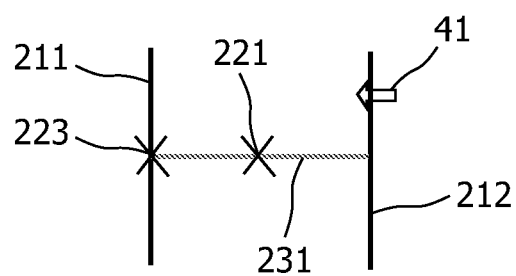
FIG. 4 schematically illustrates manipulating the caliper.
Figure 4:
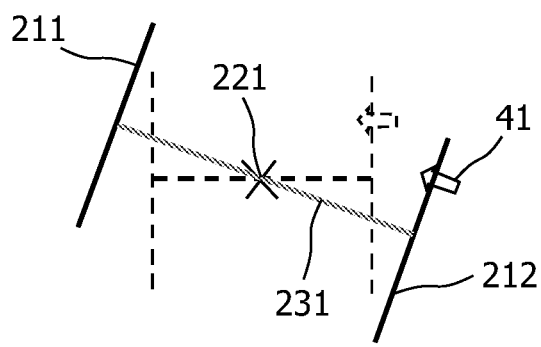
Figure 4:
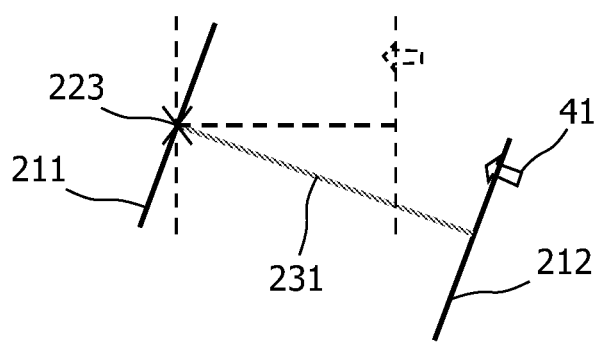

FIG. 4 schematically illustrates manipulating the caliper. The caliper in picture 400 is schematically shown in the top view. The caliper comprises the first axis 221, a third axis 223, and a line segment 231. A mouse pointer 41 is located at the second planar surface 212.

In a first implementation or mode of operation, illustrated in picture 401, the rotation axis is substantially identical with the first caliper axis 221. The first caliper axis 221 is automatically aligned with an axis of an anatomical or pathological structure, e.g., a colon polyp. Thus, only rotations and scaling are needed for manipulating the caliper. When the user places the mouse pointer over the first planar surface 211 or second planar surface 212, presses a mouse button, and moves the mouse 41, thereby dragging the selected first or second planar surface, the caliper is scaled and/or rotated about the rotation axis 221. When the user releases the mouse button, the caliper is dropped.

In a second implementation or mode of operation, illustrated in picture 402, the rotation axis is substantially identical with the third caliper axis 223, which is substantially parallel to the first caliper axis 221 and crosses an end of the line segment 231. The user may place the caliper so that the third axis is in a desired position in the image data space and scale and rotate the caliper to adjust its size and position. When the user places the mouse pointer over the second planar surface 212, presses a mouse button, and moves the mouse, thereby dragging the second planar surface 212, the caliper is scaled and/or rotated about the rotation axis 223. When the user releases the mouse button, the caliper is dropped.

Those skilled in the art will know other ways of implementing the deployment, segmentation, and/or manipulation of the caliper. The described implementations illustrate the invention and should not be construed as limiting the scope of the claims.

The caliper unit 330 of the system 300 is arranged for visualizing the caliper in the image. The caliper unit 330 is arranged to obtain data from the deployment unit 320 and/or the manipulation unit 325. Based on this data, the caliper unit 330 is further arranged to compute the image of the caliper in the image data space, for visualizing the caliper in the image. The caliper unit 330 may be a component of, or may receive data from, the image unit 310 to determine how the caliper should be located and visualized in the 3D image data space.

Figure 5:
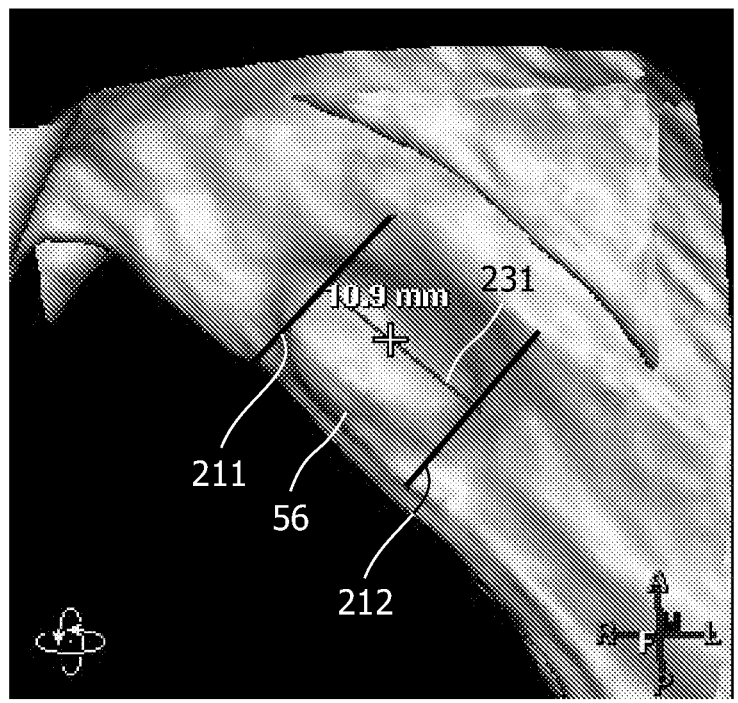
FIG. 5 shows a top view of the caliper deployed in an image data space.

FIG. 5 shows a top view of the caliper deployed in an image data space. The first axis (not visualized) of the caliper is aligned with the axis of the colon polyp 56. The alignment may be done automatically by the deployment unit 320. The line segment 231 is displayed and the center of the line segment is marked with a cross. Further, the distance between the first and second planar surface is also displayed.

Figure 6:
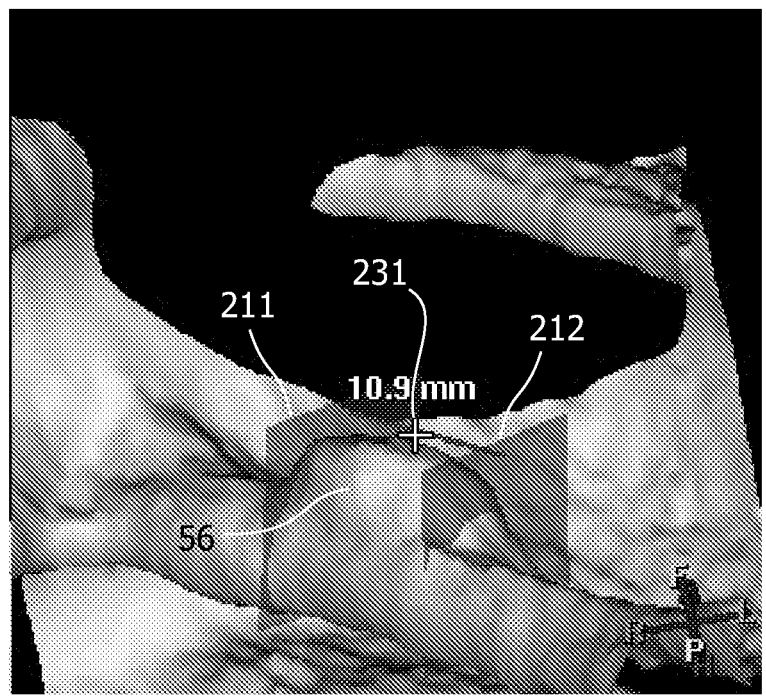
FIG. 6 shows a side view of the caliper deployed in an image data space.

FIG. 6 shows a side view of the caliper deployed in an image data space. Here too, the first axis 221 of the caliper is aligned with the axis of the colon polyp 56. The line segment 231 is displayed and the center of the line segment is marked with a cross. Further, the distance between the first and second planar surface is also displayed. The first and second planar surface 211 and 212, respectively, is semi-transparent. This allows the user to see the colon polyp and colon wall surface through the first and second planar surface. Further, parts of the first and second planar surface 211 and 212, respectively, which are behind the colon polyp and colon wall, are not visualized. This feature may be implemented based on depth buffer values of the image pixels computed from the image data by the image unit 310 and depth buffer values of caliper pixels computed by the caliper unit 330. If a depth buffer value of an image pixel is less than a depth buffer value of a caliper pixel, the image pixel value is displayed. Otherwise, the displayed pixel value is computed based on the degree of transparency of the caliper and on the image pixel value. A curve, showing where the first and second planar surface 211 and 212, respectively, cuts through the colon polyp and colon wall surface, clearly indicates what is measured. The degree of transparency of the first and second planar surface may have different values in different parts of the first and second planar surface.

Although the embodiments of the system 300 are illustrated with applications of the system 300 for performing or visualizing measurements of the colon polyp, the skilled person will understand that other applications of the system 300, e.g., to perform or visualize measurements of the diameter of a blood vessel or the size of a lung nodule, may also be useful. The described applications illustrate the invention and should not be interpreted as limiting the invention.

The skilled person will understand that other embodiments of the system 300 are also possible. It is possible, among other things, to redefine the units of the system 300 and to redistribute their functions. Although the described embodiments apply to medical images, other applications of the system 300, outside the medical domain, are also possible.

The skilled person will further recognize that the system 300 may be a valuable tool for assisting a physician in many aspects of her/his job.

The units of the system 300 may be implemented using a processor. Normally, their functions are performed under the control of a software program product. During the execution, the software program product is normally loaded into a memory, like a RAM, and executed from there. The program may be loaded from a background memory, such as a ROM, hard disk, or magnetic and/or optical storage, or may be loaded via a network like the Internet. Optionally, an application-specific integrated circuit may provide the described functionality.

Figure 7:
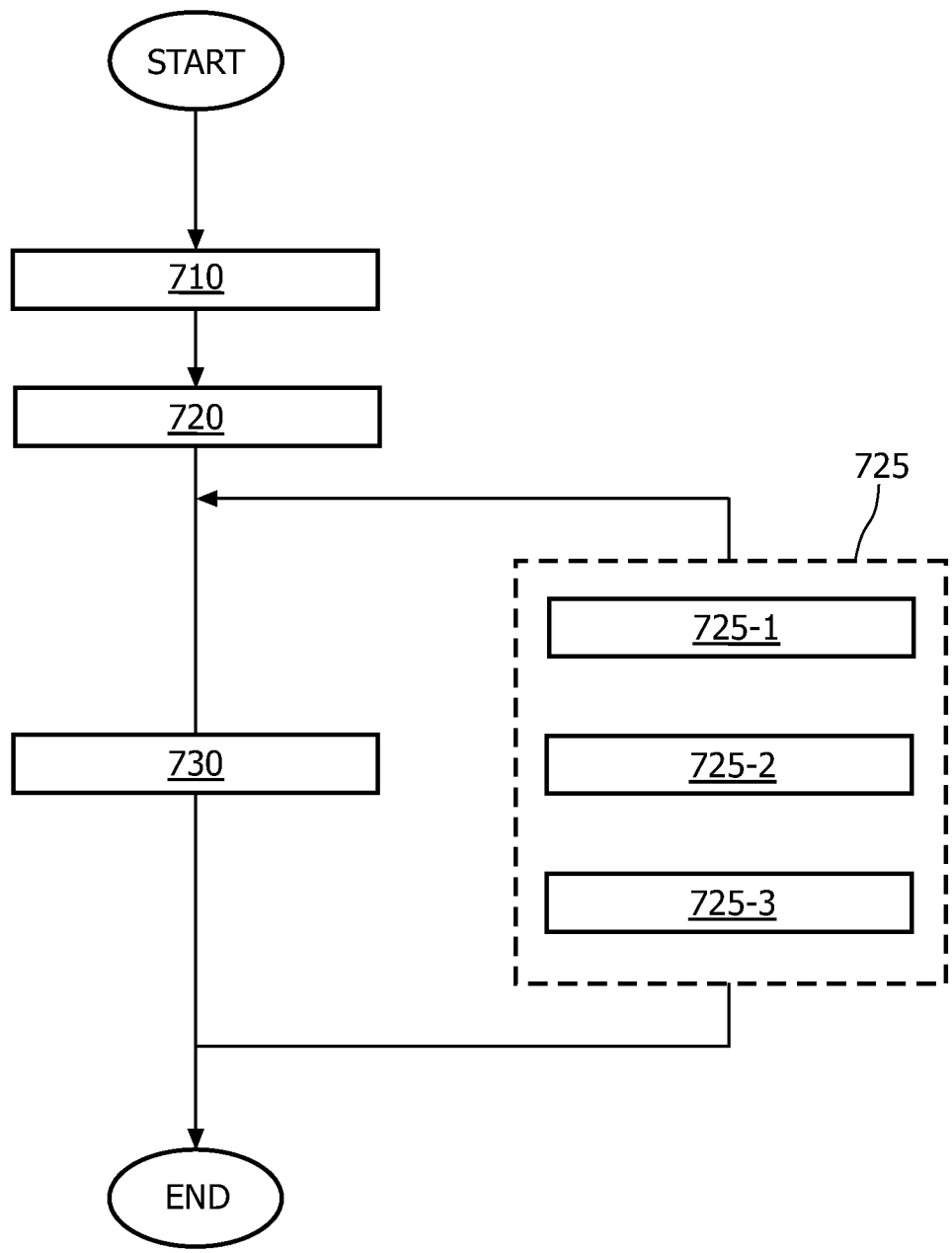
FIG. 7 shows a flowchart of an exemplary implementation of the method.

FIG. 7 shows a flowchart of an exemplary implementation of the method 700 of performing and visualizing a measurement of an object viewed in an image computed from image data. A caliper comprising a first planar surface 211 and a second planar surface 212 substantially parallel to the first planar surface is used for performing and visualizing the measurement of the object. The measured size of the object is determined based on the distance between the planes of the first and second planar surface. The method 700 begins with an image step 710 for visualizing the image data in the image for displaying in a display. After the image step 710, the method 700 continues to a deployment step 720 for deploying the caliper in an image data space based on the location of the object in the image data space. The deployment step 720 may be manual, semi-automated, or fully automated. The deployment step 720 typically comprises initializing the caliper, i.e., placing the caliper in its initial position (location and orientation) in the image data space. After the deployment step 720, the method 700 continues to a caliper step 730 for visualizing the caliper in the image. After the caliper step 730, the method 700 may continue to an optional manipulation step 725 for manipulating the caliper in the image data space, or terminates. The optional manipulation step may comprise a scaling step 725-1 for scaling the caliper in the image data space, a translation step 725-2 for manipulating the caliper in the image data space, and/or a rotation step 725-3 for rotating the caliper in the image data space. After the manipulation step 725, the method 700 returns to the caliper step 730.

The skilled person may change the order of some steps or perform some steps concurrently using threading models, multi-processor systems or multiple processes without departing from the concept as intended by the present invention. Optionally, two or more steps of the method 700 of the current invention may be combined into one step. Optionally, a step of the method 700 of the current invention may be split into a plurality of steps.

Figure 8:
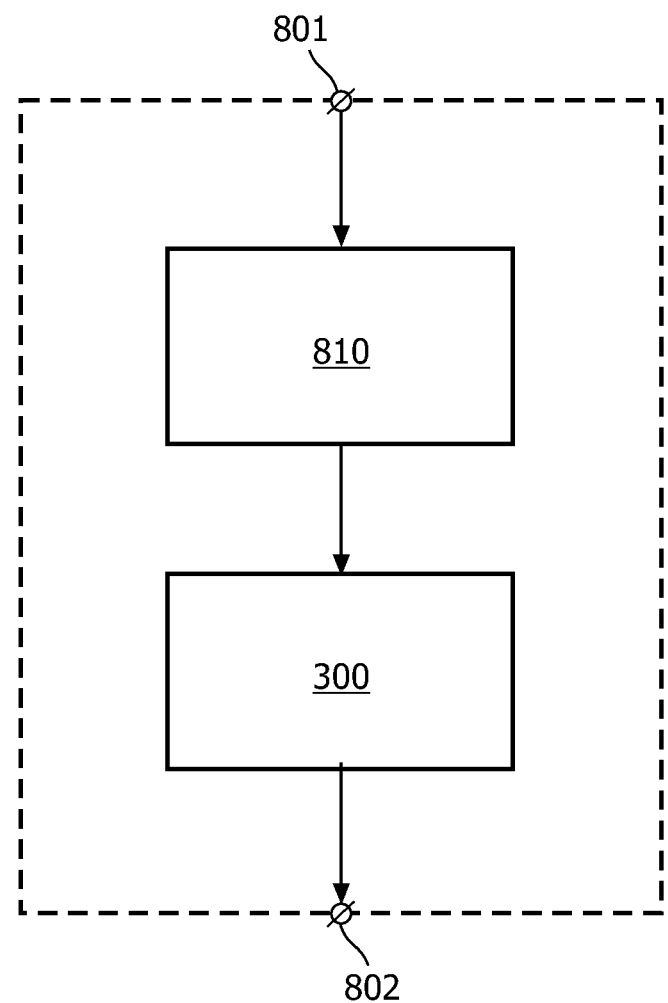
FIG. 8 schematically shows an exemplary embodiment of the image acquisition apparatus.

FIG. 8 schematically shows an exemplary embodiment of the image acquisition apparatus 800 employing the system 300, said image acquisition apparatus 800 comprising a CT image acquisition unit 810 connected via an internal connection with the system 300, an input connector 801, and an output connector 802. This arrangement advantageously increases the capabilities of the image acquisition apparatus 800, providing said image acquisition apparatus 800 with advantageous capabilities of the system 300.

Figure 9:
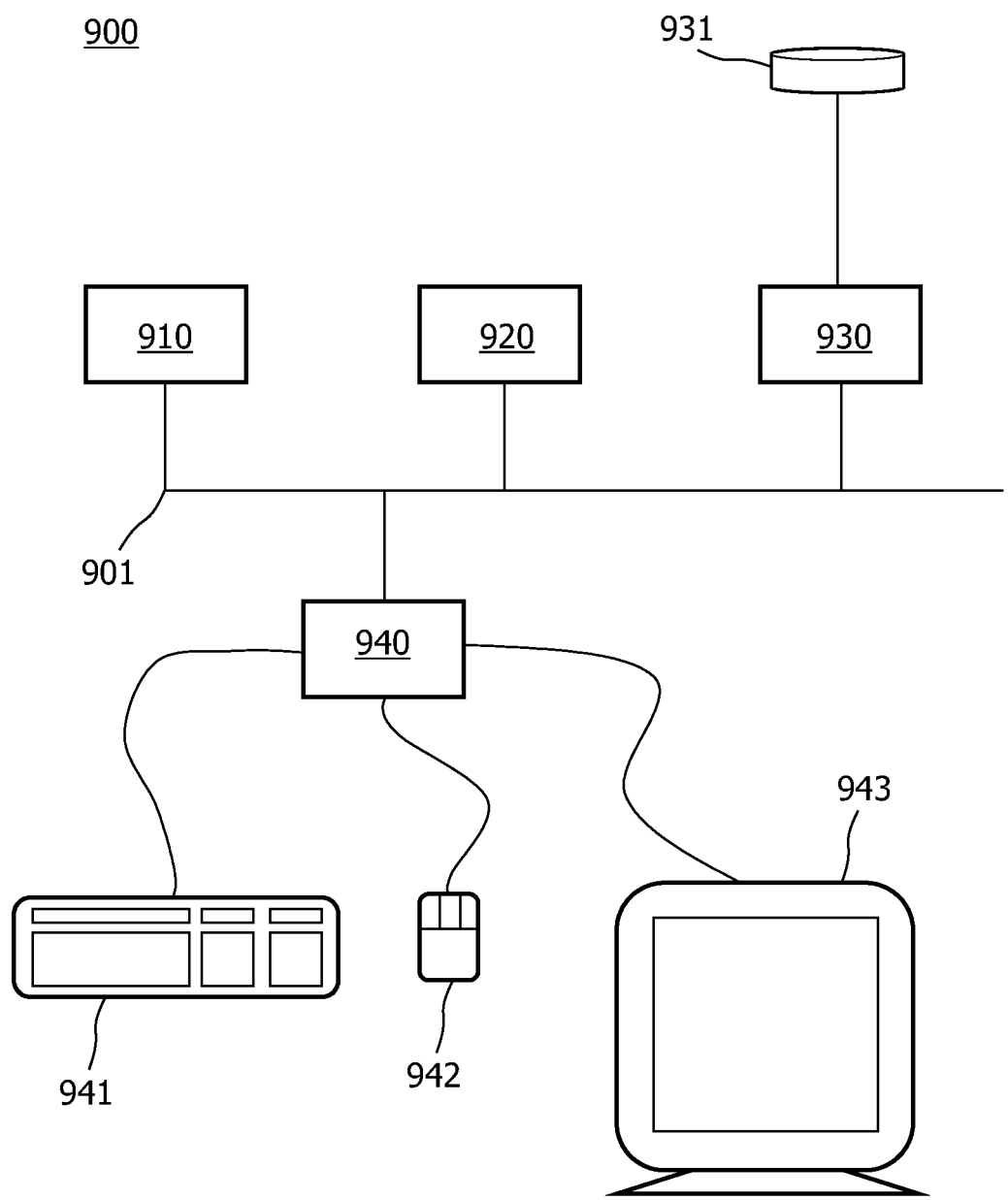
FIG. 9 schematically shows an exemplary embodiment of the workstation.

FIG. 9 schematically shows an exemplary embodiment of the workstation 900. The workstation comprises a user interface bus 901. A processor 910, a memory 920, a disk input/output (I/O) adapter 930, and a user interface (UI) 940 are operatively connected to the user interface bus 901. A disk storage device 931 is operatively coupled to the disk I/O adapter 930. A keyboard 941, a mouse 942, and a display 943 are operatively coupled to the UI 940. The system 300 of the invention, implemented as a computer program, is stored in the disk storage device 931. The workstation 900 is arranged to load the program and input data into memory 920 and execute the program on the processor 910. The user can input information to the workstation 900, using the keyboard 941 and/or the mouse 942. The workstation is arranged to output information to the display device 943 and/or to the disk 931. The skilled person will understand that there are numerous other embodiments of the workstation 900 known in the art and that the present embodiment serves the purpose of illustrating the invention and must not be interpreted as limiting the invention to this particular embodiment.

It should be noted that the above-mentioned embodiments illustrate rather than limit the invention and that those skilled in the art will be able to design alternative embodiments without departing from the scope of the appended claims. In the claims, any reference signs placed between parentheses shall not be construed as limiting the claim. The word "comprising" does not exclude the presence of elements or steps not listed in a claim or in the description. The word "a" or "an" preceding an element does not exclude the presence of a plurality of such elements. The invention can be implemented by means of hardware comprising several distinct elements and by means of a programmed computer. In the system claims enumerating several units, several of these units can be embodied by one and the same item of hardware or software. The usage of the words first, second and third, etc., does not indicate any ordering. These words are to be interpreted as names.

The invention claimed is:

1. A system for performing and visualizing a measurement of an object viewed in an image computed from image data, the system comprising:
   an image unit for visualizing the image data in the image for displaying in a display;
   a deployment unit for deploying a caliper in an image data space based on the location of the object in the image data space;
   a caliper unit for visualizing the caliper in the image; and
   a manipulation unit for manipulating the caliper in the image data space, wherein the manipulating is in response to a user input, and wherein the manipulating comprises at least one of scaling, translating, and rotating the caliper in the image;
   and further wherein the scaling may be isotropic, anisotropic, or directional;
   wherein the caliper comprises a first planar surface and a second planar surface substantially parallel to the first planar surface,
   wherein the deployment unit further comprises the first and second planar surfaces which are rotatable in three-dimensional space about a selected axis,
   wherein the measurement of the object is determined based on the distance between the planes of the first and second planar surface, and wherein the caliper unit visualizes the caliper by computing an image of the caliper using data from at least the deployment unit or the manipulation unit.

2. A system as claimed in claim 1, wherein the first or second planar surface is semi-transparent.

3. A system as claimed in claim 1, wherein the caliper further comprises a caliper axis.

4. A system as claimed in claim 3, wherein the deployment unit is further arranged for aligning the caliper axis with an axis of the object.

5. A system as claimed in claim 1, for measuring a colon polyp in a colonoscopic CT image.

6. An image acquisition apparatus comprising a system as claimed in claim 1.

7. A workstation comprising a system as claimed in claim 1.

8. A method of performing and visualizing a measurement of an object viewed in an image computed from image data, the method comprising:
- an image step for visualizing the image data in the image for displaying in a display;
- a deployment step for deploying a caliper in an image data space based on the location of the object in the image data space;
- a caliper step for visualizing the caliper in the image; and
- a manipulating step for manipulating the caliper in the image data space, in response to a user input, wherein the manipulating comprises at least one of scaling, translating, and rotating the caliper in the image; and
  - further wherein the scaling may be isotropic, anisotropic, or directional;
- wherein the caliper comprises a first planar surface and a second planar surface substantially parallel to the first planar surface,
- wherein the first and second planar surfaces are rotatable in three-dimensional space about a selected axis,
- wherein the measurement of the object is determined based on the distance between the planes of the first and second planar surface, and
- wherein the caliper unit visualizes the caliper by computing an image of the caliper using data from at least the deployment unit or the manipulation unit.

9. A computer program product embodied on a non-transitory computer readable medium, comprising instructions for performing and visualizing a measurement of an object viewed in an image computed from image data, the computer arrangement comprising a processing unit and a memory, the computer program product, after being loaded, providing said processing unit with the capability to carry out the tasks of:
- visualizing the image data in the image for displaying in a display;
- deploying a caliper in an image data space based on the location of the object in the image data space;
- visualizing the caliper in the image; and
- manipulating the caliper in the image data space, in response to a user input, wherein the manipulating comprises at least one of scaling, translating, and rotating the caliper in the image; and
  - further wherein the scaling may be isotropic, anisotropic, or directional;
- wherein the caliper comprises a first planar surface and a second planar surface substantially parallel to the first planar surface,
- wherein the first and second planar surfaces are rotatable in three-dimensional space about a selected axis,
- wherein the measurement of the object is determined based on the distance between the planes of the first and second planar surface, and
- wherein the caliper unit visualizes the caliper by computing an image of the caliper using data from at least the deployment unit or the manipulation unit.

* * * * *